US 8,784,892 B2

United States Patent
Touitou

(10) Patent No.: US 8,784,892 B2
(45) Date of Patent: Jul. 22, 2014

(54) METHOD AND COMPOSITION FOR BURNED SKIN

(75) Inventor: Elka Touitou, Jerusalem (IL)

(73) Assignee: Yissum Research Development Company of the Hebrew University of Jerusalem, Givat Ram (IL)

(*) Notice: Subject to any disclaimer, the term of this patent is extended or adjusted under 35 U.S.C. 154(b) by 0 days.

(21) Appl. No.: 12/831,349

(22) Filed: Jul. 7, 2010

(65) Prior Publication Data
US 2011/0111010 A1 May 12, 2011

Related U.S. Application Data

(63) Continuation of application No. 10/591,687, filed as application No. PCT/IL2005/000249 on Mar. 3, 2005, now abandoned, which is a continuation-in-part of application No. 10/791,782, filed on Mar. 4, 2004, now abandoned.

(51) Int. Cl.
| | |
|---|---|
| *A61K 9/14* | (2006.01) |
| *A61K 31/045* | (2006.01) |
| *A61K 31/445* | (2006.01) |
| *A61K 31/515* | (2006.01) |
| *A61K 31/24* | (2006.01) |
| *A61K 31/02* | (2006.01) |
| *A61K 31/46* | (2006.01) |

(52) U.S. Cl.
USPC ........... 424/487; 514/724; 514/327; 514/270; 514/536; 514/304; 514/758

(58) Field of Classification Search
USPC .......... 424/487; 514/724, 327, 270, 536, 304, 514/758
See application file for complete search history.

(56) References Cited

U.S. PATENT DOCUMENTS

| | | | |
|---|---|---|---|
| 5,013,545 A | 5/1991 | Blackman et al. | |
| 5,122,374 A | 6/1992 | Dupoy de Guitard et al. | |
| 5,447,930 A | 9/1995 | Nayak | |
| 5,604,200 A | 2/1997 | Taylor-McCord | |
| 5,958,420 A * | 9/1999 | Jenson | 424/771 |
| 6,071,959 A * | 6/2000 | Rhodes et al. | 514/535 |
| 6,656,928 B1 | 12/2003 | McCadden | |
| 2002/0037977 A1* | 3/2002 | Feldstein et al. | 526/60 |
| 2003/0027833 A1* | 2/2003 | Cleary et al. | 514/270 |

FOREIGN PATENT DOCUMENTS

| | | |
|---|---|---|
| EP | 0 320 254 | 6/1989 |
| EP | 0 439 344 | 7/1991 |
| JP | H03-502792 | 6/1991 |
| JP | H04-500804 | 2/1992 |

(Continued)

OTHER PUBLICATIONS

"Industrial First Aid/Burn Cream", online, Feb. 13, 2004 (URL: http://web.archive.org/web/20040213160601/http://www.first-aid-store.com/industrial/first-aid-burn-cream.htm>).

(Continued)

*Primary Examiner* — Ernst Arnold
*Assistant Examiner* — Hong Yu
(74) *Attorney, Agent, or Firm* — Browdy and Neimark, PLLC

(57) ABSTRACT

The present invention is directed to the use of an agent selected from ethyl alcohol, isopropyl alcohol or a mixture thereof and a topically acceptable polymeric carrier in the preparation of a composition for the treatment of burns.

26 Claims, 5 Drawing Sheets

(56) References Cited

FOREIGN PATENT DOCUMENTS

| | | |
|---|---|---|
| JP | 4-210914 | 8/1992 |
| JP | 4-309535 | 11/1992 |
| JP | 7-97327 | 4/1995 |
| JP | 7-250859 | 10/1995 |
| JP | 2002-514220 | 5/2002 |
| JP | 2003-535131 | 11/2003 |
| WO | 89/07436 | 8/1989 |
| WO | 90/03166 | 4/1990 |
| WO | 98/51273 | 11/1998 |
| WO | 01/93857 | 12/2001 |

OTHER PUBLICATIONS

Plazier-Vercammen J et al., "Rheological Properties of Carbopol 950 and 954 Neutralized with Triethanolamine and Neutrol TE (R)", Pharmazie, Die, Pharmazeutischer Verl., 46(9), 1991, pp. 646-650.

Hunter et al., Effects of Isopropyl Alcohol, Ethanol, and Polyethylene Glycol/Industrial Methylated Spirits in the Treatment of Acute Phenol Burns, Annals of Emergency Medicine, Pub. Apr. 18, 1991, pp. 11-15.

Stretton, "Burn Treated with Ethyl Alcohol," Letters to the Editor, Burns, 1994, 20(2), 186-187.

* cited by examiner

Fig 1A
Fig 1B
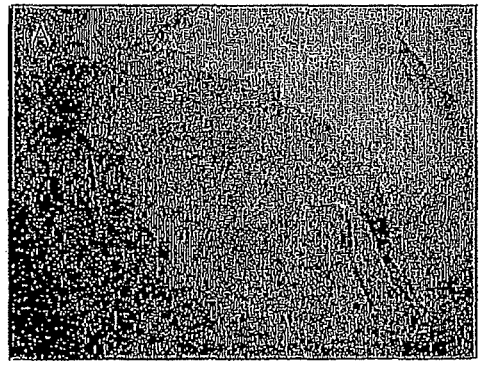
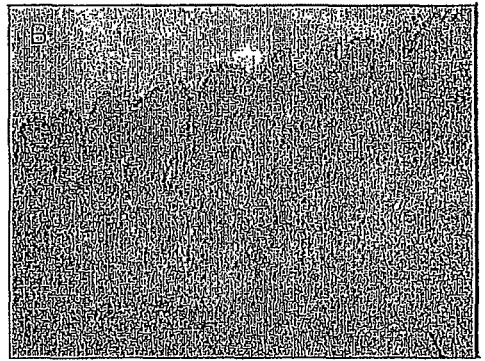
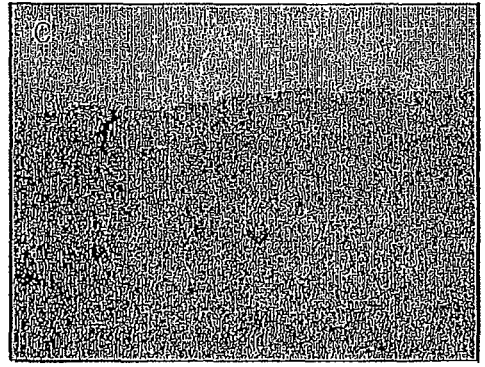
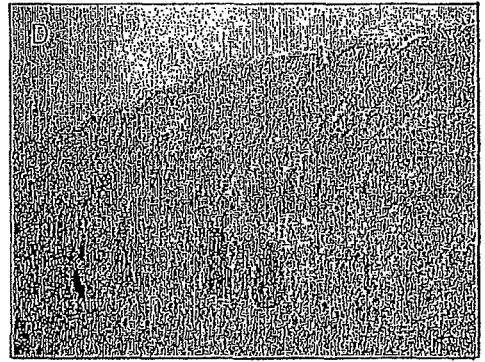
Fig 1C
Fig 1D

METHOD AND COMPOSITION FOR BURNED SKIN

CROSS-REFERENCE TO RELATED APPLICATIONS

This application is a continuation of U.S. patent application Ser. No. 10/591,687, filed Jun. 5, 2007, which is the U.S. national stage of International Application No. PCT/IL2005/000249, filed Mar. 3, 2005, which claims priority to U.S. patent application Ser. No. 10/791,782, filed, Mar. 4, 2004 (abandoned), the entire contents of each of which are hereby incorporated by reference.

FIELD OF THE INVENTION

This invention relates to compositions comprising ethanol and/or isopropanol and a suitable carrier for the treatment of burns.

BACKGROUND OF THE INVENTION

Thermal burn injury induces non-specific inflammatory reaction generating dermal vascular damage, destruction of epidermis, edema and blister formation. These responses lead to progressive ischemic damage to the skin tissue, reduced blood perfusion and tissue necrosis. Since not all the skin tissues are immediately destroyed after thermal burn, depth of burns progresses with time. Cytokines IL6, IL1 TNF alpha, other pro-inflammatory interleukins and globulins are important factors in the development of microvascular injury and wound development in burned skin and tissue. Numerous attempts to favorably alter the burn wound by pharmacologic agent are generally of moderate efficiency. Burned skin could be a result of infliction produced by heat, light, UV rays, X-rays, Laser, Infrared rays, friction, abrasion, cold, liquid nitrogen.

The use of anti-inflammatory agents and local anesthetics to alleviate inflammation and pain resulting from burns is known. Compositions containing steroidal anti-inflammatories, non-steroidal anti-inflammatories, as well as "natural" anti-inflammatories, such as extract of plants such as aloe vera, have been used.

With respect to the care of burns, the main objectives are to relieve pain, help prevent contamination, eliminate the source of heat and stop the burn progress.

BRIEF DESCRIPTION OF THE DRAWINGS

FIG. 1 (A-D) demonstrates histological images of rat skin sections following in vivo treatment after thermal burn: (A) Control-no treatment, t=24 hours; (B) immediate application of the composition, t=3 hours; (C) non-immediate treatment (delayed for 1 hour after burn) t=24 hours; and (D) immediate application of the composition, t=24.

SUMMARY OF THE INVENTION

Figure 2:
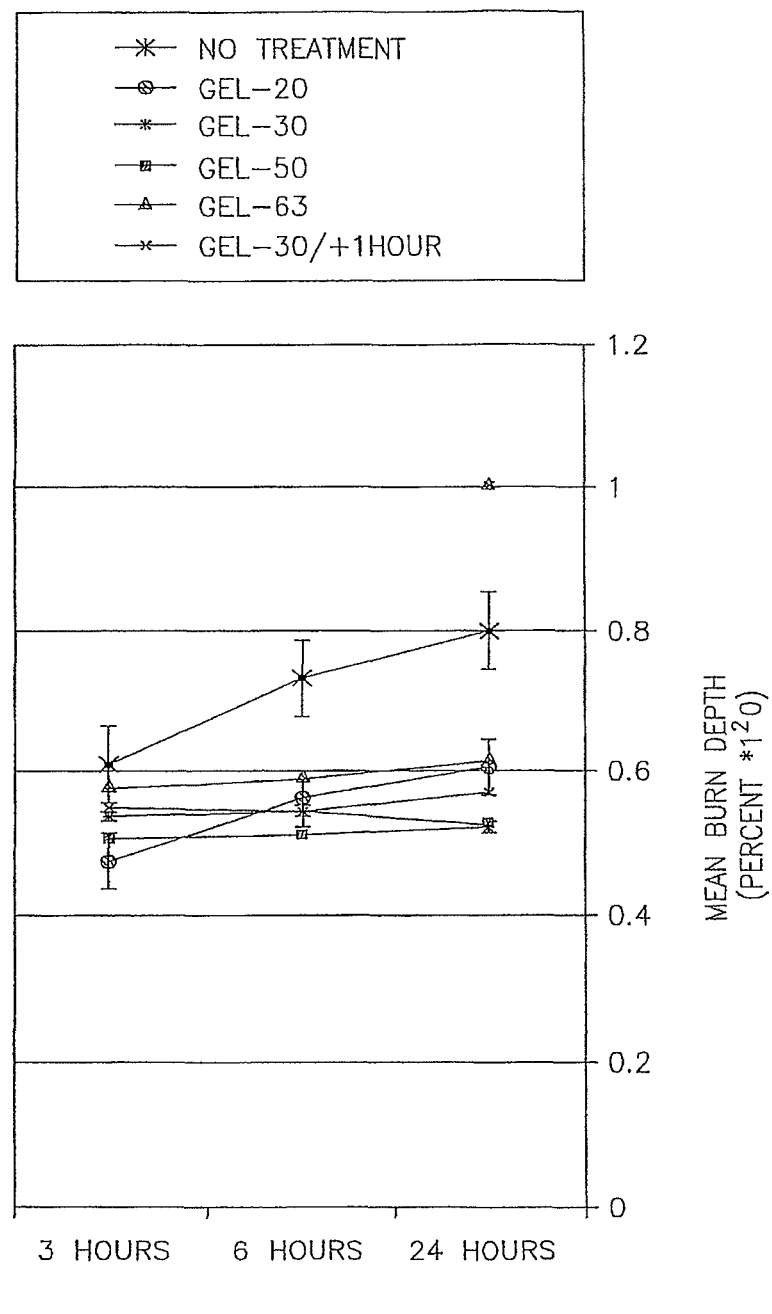
FIG. 2 demonstrates measurement of depth dermal microvascular destruction 24 hours after burn infliction: Animals have been treated immediately after infliction with CARBOPOL® gels containing 4% ammonium hydroxide 10% aqueous solution and 20, 30, 50 and 63% w/w ethanol and 1 hour after infliction with a gel containing 30% ethanol. The results were compared with untreated inflicted rates. The depth parameter was measured in rats sacrificed 3, 6, and 24 hours after burn infliction.

In a first aspect, the present invention relates to the use of an agent selected from ethyl alcohol, isopropyl alcohol or a mixture thereof and a topically acceptable polymeric carrier in the preparation of a composition for treatment of burns.

The term "treatment", as used herein, refers to at least one of the following: prevention of burn development after skin contact with a burn-forming condition, prevention of vesicle formation after skin contact with burn forming condition, decrease in the size of the burn formed as compared to untreated control, decrease in the severity of the burn (typically as defined by burn grade) as compared with untreated control, increase in the speed of healing of the burn, decrease in pain or scarring produced by the burn or a combination of two or more of the above.

The term "burn", as used herein, refers to a damage caused to the skin, including at least the epidermis, followed by edema, inflammation cell migration and destruction of the integrity of at least one skin layer (epidermis, basal, collagen) by contact of the skin with a "burn forming condition". This condition may be extreme heat, cold or irradiation, specifically laser irradiation.

A particularly suitable topically acceptable carrier which may be used in the preparation of the composition according to the invention comprises a polymer which forms a gel like matrix with the alcohol(s). One or more acidic polymers, and more preferably, polymers containing acrylic groups may be suitably applied to this end, wherein said acrylic polymers (for example, CARBOPOL®) are most preferably present in the composition of the invention in a neutralized form, in order to render the composition sufficiently viscous.

The neutralized form of the acidic polymer serving as a carrier according to the present invention is obtained by introducing an alkaline agent thereto. Suitable alkaline agents include both inorganic and organic bases, with nitrogen containing bases being more preferred. Ammonium hydroxide and amine derivatives, such as di- and trialklanolamines (e.g., triethanolamine), are particularly preferred.

The concentration of the alcohol(s) in the composition of the invention is preferably in the range of 15 to 65%, and more preferably in the range 20 to 50%, and most preferably in the range of 20 to 40% of the total weight of the composition. Suitable concentrations of the acrylic polymer and the alkaline agent used for neutralizing the same in the composition of the invention are in the ranges of 0.05 to 5% and 0.1 to 10%, respectively.

A particularly preferred ethanol-containing composition for use in the treatment of burns, as provided by the present invention, comprises ethanol in a concentration of 15-65% w/w, polyacrylate polymer in a concentration of 0.05%-5% and ammonium hydroxide in a concentration of 0.1-10%. Another preferred composition according to the invention comprises ethanol in a concentration of 25-65% w/w, polyacrylate in a concentration of 0.05%-5% and triethanolamine in a concentration of 0.1-6%

Alternative polymers which may be used for formulating ethanol, isopropanol or a mixture thereof to afford a topically acceptable composition that may be suitably used for the treatment of burns may be selected from the following group:

chitin, guar, chitsan, polyvinylpyrrolidone, polyvinylalcohol, gum, sylastic, eudragit, pectin, hyaluronic acid, hyaluronate, gelatin, gelatin deriviative, agar, adhesive polymers, cellulose or derivatives thereof, including methylcelluose, ethylcellulose, hydroxypropylcellulose, hydroxyethylcellulose, or a mixture of the aforementioned excipients.

Additional agents that may be advantageously included in the composition of the invention are urea and plants-derived materials, which are preferably in the form of plant extracts, tinctures, oils and/or macerates. The plant may be preferably selected from the group consisting of *arnica, plantago, equisetum*, lavender, joubabe, *hamamelis, urtica, calendula, daucus, symphytum, sanguisorba, symphytum, aloe vera*, roman chamomile, tea tree, witch hazel and *mameluca*.

The composition according to the invention may also comprise one or more ingredients selected from the group consisting of a local anesthetic, antibiotic, plant extract, vitamin, growth factor, protein, histamine, carnosine, insulin, anti-inflammatory agent, antiseptic agent, antifungal agent, anti-cytokine, an interleukin, growth hormone and re-epithelization factors.

The composition according to the present invention may be provided in any suitable form, including a gel, cream, emulsion, lotion, suspension, liposomes, ethosomes, microcapsules or microspheres.

DETAILED EMBODIMENTS OF THE INVENTION

According to a preferred embodiment, the invention relates to the use of ethanol and/or isopropanol for the treatment of burns, wherein said alcohol(s) are delivered to the targeted area by means of a suitable carrier capable of forming a gel like matrix with said alcohol(s). It has been found that a composition in which the alcohol(s) are present in a thickened, gelled form is effective for treating burns even at a relatively low concentration of said alcohols (that is, at about 15 to 65%, and more preferably, at about 20 to 40% of the total weight of the composition).

In general, the polymer, which is preferably an acidic polymer provided in a powdery form, and more preferably, an acrylic polymer (CARBOPOL®), is dispersed under stirring in the alcoholic (most preferably ethanol) solution. Preferably, a suitable quantity of a neutralizing agent, which is either an inorganic or organic base (sodium hydroxide, potassium hydroxide, a nitrogen containing base selected from the group of ammonium hydroxide and di- or tri alkanolamines, such as triethanolamine) is added under continuous stirring into the mixture, whereupon the polymer is transformed into the corresponding salt and the viscosity of the mixture is increased, and gel is formed. Additional ingredients that may be suitably included in the composition may be mixed with the polymer powder before adding the same into the alcoholic solution, or may be introduced into the mixture after gel formation.

The composition or the delivery system may further include other agents, such as for example without limitation, an antibiotic, a plant extract, a local anesthetic.

In another embodiment, the composition or the delivery system further comprises plant extracts/tinctures/oils/macerates such is *arnica, plantago, equisetum*, lavender, joubarbe, *hamamelis, urtica, calendula, daucus, symphytum, sanguisorba, aloe vera*, roman chamomile, tea tree, witch hazel, *mameluca*, emu, *Celosia Argentea*.

The composition can also contain antimicrobials including antibiotics, sulpha derivatives, silver sulphadiazine and mafenide, antifungals, iodine, anti-viral compounds and other which may complement or supplement the activity of the basic composition. Suitable antibiotics include tetracycline, polymyxin, erythromycin, bacitracin, gentamycin, vincomycin, clindamyicin, or other antibiotics used in topical or systemic administration, including over-the-counter formulations. Examples of useful antifungals include tolnaftate, nystatin, micatin.

Examples of antivirals include interferon, either natural or recombinant, as well as nucleoside analogs, e.g., acyclovir. Counter-irritants such as camphor and menthol, drying agents such as benzyl alcohol, resorcinol and phenol, and astringents such as zinc sulfate and tannins can also be added to the composition as can other types of agents such as sunscreens, emollients, preservatives, fragrances, antioxidants, color additives, lubricants, moisturizers or drying agents. For example, sunscreens, can be added to the formula for burns caused by ultraviolet radiation.

Examples of antibiotics include: chloramphenicol, chlortetracycline, clindamycin, clioquinol, erythromycin, framycetin, gramicidin, fusidic acid, gentamicin, mafenide, mupiroicin, neomycin, polymyxin B, bacitracin, silver sulfadiazine, tetracycline and chlortetracycline, steroidal antibiotics, tobramicyn, peptide antibiotics, CSAs that act against gram-negative and gram-positive bacteria. Those of ordinary skill in the art will appreciate that there are other appropriate antibiotics such as those listed in the pharmaceutical formularies or new antibiotic molecules.

In another embodiment, the composition or the delivery system may include Tea Tree Blend. Tea Tree Blend is a mixture of terpenes and terpinols that are generally naturally occurring, but can be synthetically prepared. The terpene and terpinol compounds can be obtained either as pure compounds derived from the natural oils or as mixtures of components derived from plants of *Melaleuca alternifolia, Melaleuca lineariifolia, Melaleuca leucadendron, Eucalyptus longirostris* and closely related species.

In another embodiment, a local anesthetic may be added. The anesthetic is preferably selected from the group consisting of esters, amides, ethers, and combinations thereof and, in particular, anesthetics and other anesthetics which may be formulated in accordance with the preferred embodiments of the present invention and applied, including procaine, chloroprocaine, tetracaine, propoxycaine, benzocaine, cocaine, proparacaine, bupivacaine, dibucaine, etidocaine, lidocaine, mepivacaine, prilocalne, dyclonine, promazine and combinations thereof.

Anti-inflammatory actives useful in accordance with the present invention include steroidal actives such as hydrocortisone as well as non-steroidal actives including propionic derivatives; acetic acid derivatives; biphenylcarboxylic acid derivatives; fenamic acid derivatives; and oxicams. Examples of anti-inflammatory actives include without limitation acetaminophen, diclofenac, diclofenac sodium and other salts, ibuprofen and its salts acetaminophen, indomethacin, oxaprozin, pranoprofen, benoxaprofen, bucloxic acid, elocon; and mixtures thereof.

Vitamin actives which may be used in accordance with the present invention include vitamin A and derivatives, including retinoic acid, retinyl aldehyde, retin A, retinyl palmitate, adapalene, and beta-carotene; vitamin B (panthenol, provitamin B5, panthenic acid, vitamin B complex factor); vitamin C (ascorbic acid and salts thereof) and derivatives such as ascorbyl palmitate; vitamin D including calcipotriene (a vitamin D3 analog) vitamin E including its individual constituents alpha-, beta-, gamma-, delta-tocopherol and cotrienols and mixtures thereof and vitamin E derivatives including vitamin E palmitate, vitamin E linolate and vitamin E acetate; vitamin K and derivatives; vitamin Q (ubiquinone) and mixtures thereof.

The composition may also contain one or more additional agents, including, buffering agents, surfactants, antioxidants, permeation enhancing agents, preservatives, parabens, coloring agents, fragrances, lubricants, moisturizers, sunscreens, drying agents and the like. The surfactant may be selected from the group consisting of anionic, nonionic, and cationic surfactants and combinations thereof. Suitable ionic surfactants include anionic surfactants such as monovalent salts, e.g., sodium and potassium salts of alkyl, aryl and alkyl-aryl sulfates and sulfonates, particularly those with from about 8 to 22 carbon atoms, and cationic surfactants, such as quaternary ammonium salts. Suitable non-ionic surfactants include, sorbitan esters, polyoxyethylene sorbitan esthers, PEG alky ethers, PEG alky esthers, polyethylene oxide adducts of fatty alcohols, alkylated polyoxyethylenes, alkylated polyoxyethylene-polyoxypropylene copolymers, sugar surfactants.

In addition, cationic surfactants may be used, alone. An example is trimethyldodecylammonium chloride, a positively charged quaternary ammonium complex that has antimicrobial characteristics. Other quaternary salts, with and without long chain moieties to provide surface activity.

Nonionic surfactants such as polysorbates, nonoxynol, polyoxyethylene alkyl ethers, polyoxyethylene alkyl ethers, sorbitan esters. Other common nonionic surfactants include polyoxyethylenes amines and polyoxyethylenes amides, polyoxyethylene-polyoxypropylene copolymers, alkyl sorbitols.

Generally, the formulation could take several forms, e.g., cream, gel, spray, ointment, "Chapstick" and solution forms. Each of these formulations may contain the two active ingredients as well as microorganism growth inhibitors (preservatives). Many such carriers are routinely used and can be obtained by reference to pharmaceutical texts. Examples include polyethylene glycols (PEG), polypropylene copolymers (Pluronics), and some water soluble gels.

Thickeners could include natural and synthetic types. The thickeners used can include but are not limited to xanthan, karaya, guar gum, clay tragacanth various polysaccharide materials such as starches. The thickeners can be present in an amount of about 0 parts to about 5 parts.

Preservative or preservatives are selected from the group consisting of phenoxyethanol, methylparaben, propylparaben, benzyl alcohol, benzoic acid, sodium benzoate, potassium benzoate, sorbic acid, sodium sorbate, potassium sorbate and phenylethyl alcohol, DMDM hydantoin, iodopropylbutylcarbamate, borax.

Another ingredient, which may be formulated with the compositions of the present invention, is a moisturizer. As used herein a "moisturizer" is an ingredient, which promotes the retention of water to the surface area of the human body skin. The term moisturizer as used herein includes both components that deliver water to the skin, also commonly referred to in the art as "humectant". Moisturizers that may used in accordance with the present invention include without limitation polyhydroxy alcohols, including glycerol, butylene glycol, hexylene glycol, propylene glycol, tetraglycol, sorbitol and the like; lactic acid and lactate salts, such as sodium or ammonium salts; $C_3$ and $C_6$ diols and triols including hexylene glycol, 1,4 dihydroxyhexane, 1,2,6-hexane triol; aloe vera in any of its forms, for example aloe vera gel; sugars and starches; sugar and starch derivatives, for example alkoxylated glucose; hyaluronic acid; lactamide monoethanolamine; acetamide monoethanolamine; glycolic acid; alpha and beta hydroxy acids (e.g. lactic, glycolic salicylic acid).

A further ingredient, which may be formulated with the compositions of the present invention, is an emollient. Emollients are used to add or replace lipids and natural oils to the surface area of the human body. Emollients which may be used in the present invention may be selected from the group consisting of natural oils and plant-derived and essential oils, esters, silicone oils, polyunsaturated fatty acids, lanoline and its derivatives.

Further useful emollients include silicone oils, including non-volatile and volatile silicones. Examples of silicone oils that may be used in the compositions of the present invention are dimethicone; cyclomethycone; dimethycone-copolyol; aminofunctional silicones; phenyl modified silicones; alklyl modified silicones; dimethyl and diethyl polysiloxane; mixed C1-C30 alkyl polysiloxane; and mixtures thereof.

It is noted that although the ingredients mentioned herein are generally defined as emollients they may also possess other properties such as moisturization or other conditioning properties (see under: Moisturizers, hereinbefore mentioned).

In an embodiment of the invention the composition may comprise ethanol from 20-60% w/w, polyacrylate polymer from 0.05%-5%, ammonium hydroxide from 0.1-10%, water from 30-79% to be applied on burned skin and surrounding area, to treat/impede progression/impede development of burns, scalds (produced by heat, hot vapors, cold, light, uv rays, x rays, Laser, Infrared Rays, liquid nitrogen).

In another embodiment of the invention, the composition may comprise ethanol from 25-60% w/w, polyacrylate polymer from 0.05%-5% w/w triethanolamine from 0.1-6%, water from 30-75%, to treat/impede progression/impede development of burns, scalds (produced by heat, hot vapors, cold, light, UV rays, X-Rays, Laser, Infrared Rays, friction, abrasion, liquid nitrogen).

In another embodiment the composition may comprise ethanol from 15-60% w/w, polyacrylate polymer from 0.05%-5%, ammonium hydroxide from 0.1-10%, urea from 0.05 to 5% and water from 30-84%, to treat/impede progression/impede development of burns, scalds (produced by heat, vapors, cold, light, UV rays, X-Rays, Laser, Infrared Rays, liquid nitrogen).

The composition or the delivery system of the invention may be in a form of gel, cream, emulsion, lotion, suspension, liposomes, ethosomes, microcapsules and microspheres. The composition may be applied onto the skin by means of a bandage, perforated bandage, burn dressing, patch, spray, bath, brushing, douches, aerosols, jet aerosols and foams.

It is another object of the present invention to provide a method of avoiding or minimizing burn damage to the skin by applying to the burned area the composition of the invention, as described hereinabove. Accordingly, the invention provides use of the composition described hereinabove for treating and/or impedes progression and/or impedes development of burns.

In another aspect, the present invention provides a method of avoiding or minimizing burn damage to the skin.

In one embodiment, the treatment is a one stage treatment by the compositions/devices that stop burn progression and facilitate healing (re-epithelization, re-vascularisation, etc.

In another embodiment, the treatment may comprise two stages treatment: Stage I—treatment for impeding/stopping wound formation/burn progression/burn development; Stage II—treatment for healing-re-epithelization.

In another embodiment, the invention provides delivery systems that could impede wound development, which comprise short chain volatile alcohols such as ethanol and isopropyl alcohol with or without additional agents, applied on burned skin, surrounding skin, membrane or organ, before or after burn stimulus.

In another embodiment, the invention provides a method for treating and/or impeding progression and/or impeding development of burns comprising the step of adding to the burned area a composition comprising ethyl or isopropyl alcohol in a concentration of 20-65% w/w.

In another embodiment, the invention provides a method for treating and/or impeding progression and/or impeding development of burns comprising the step of adding a composition to the burned area comprising ammonium hydroxide.

In another embodiment, the invention provides a method for treating and/or impeding progression and/or impeding development of burns comprising the step of adding to the burned area a composition comprising ammonium hydroxide and ethyl and/or isopropyl alcohol wherein the ethyl and/or isopropyl is in a concentration of 20-60% w/w.

In another embodiment, the invention provides a method for treating and/or impeding progression and/or impede development of burns comprising the step of adding to the burned area a delivery system comprising polymer matrix and ethyl or isopropyl alcohol in a concentration of 20-60% w/w.

In another embodiment, the invention provides a method for treating and/or impeding progression and/or impeding development of burns comprising the step of adding a delivery system comprising polymer matrix and ammonium hydroxide.

In another embodiment, the invention provides a method for treating and/or impede progression and/or impede development of burns comprising the step of adding to the burned area a delivery system comprising a polymer matrix, ammonium hydroxide and ethyl and/or isopropyl alcohol wherein the ethyl and/or isopropyl is in a concentration of 20-65% w/w.

In another embodiment, the invention provides a method for treating and/or impeding progression and/or impeding development of burns comprising the step of adding to the burned area a composition comprising ethanol from 20-65% w/w, polyacrylate polymer from 0.05%-5%, ammonium hydroxide from 0.1-10%, water from 30-80% to be applied on burned skin and surrounding area, to treat an or impede progression and or impede development of burns.

In another embodiment, the invention provides a method for treating and/or impeding progression and or impeding development of burns comprising the step of adding to the burned area a composition comprising ethanol from 25-60% w/w, polyacrylate polymer from 0.05%-5% w/w, triethanolamine from 0.1-6%, water from 30-74%, to be applied on burned skin and surrounding area, to treat an or impede progression and or impede development of burns.

In another embodiment, the invention provides a method for treating and/or impeding progression and/or impeding development of burns comprising the step of adding to the burned area a composition comprising ethanol from 15-60% w/w, polyacrylate polymer from 0.05%-5%, ammonium hydroxide from 0.1-10%, urea from 0.05 to 5% and water from 30-84%, to be applied on burned skin and surrounding area, to treat an or impede progression and or impede development of burns.

In another embodiment of the invention, there is provided a method for interfering at the infliction site with production of cytokines, interleukins, tumor necrosis factors, IL1, IL6, TNF, comprising the step of contact of the inflicted area and the surrounding area with an effective amount of the composition of the invention.

In another embodiment of the invention, the composition and the delivery system described above are refrigerated before or during use.

In another embodiment of the invention, the compositions and the delivery systems described above are sterilized before use.

In another embodiment, the invention provides a method for treating and/or impede progression and/or impede development of burns comprising the step of adding to the burned area the above described compositions as thick layers on the inflicted skin area.

The topical compositions are administered by applying a therapeutically-effective amount of the alcohol-containing gel to the skin site to be treated. A "therapeutically-effective amount" of the compositions of the present invention may be defined as any weight of the composition that contains an amount of alcohol that is judged by the prescribing physician or other health care professional to be sufficient to produce the desired therapeutic effect, either as a single dose, or when repeated in a multiple-dose regime. Generally, however, it is necessary to apply between 20 mg/cm.sup.2 to 2 g/cm.sup.2 of a composition of the present invention. This dosage may then be repeated several times per day, in accordance with the health care professional's instructions.

EXAMPLES

Example 1

Carbomer Gelled Matrix Containing Ethanol 35% w/w

|  | % w/w |
| --- | --- |
| Ethanol | 35 |
| Ammonium hydroxide sol (10%) | 4 |
| CARBOPOL ® 940 | 2.2 |
| Water for injection | to 100 |

The preparation was kept refrigerated (+4 degrees Celsius) until use.

Composition 1 was applied to a second degree burn (as a result of short contact with 175.degree. C. hot oven) on the skin of left hand of a 30 years aged female and remained on the skin for about one hour. This treatment completely impeded the development of the burn.

Example 2

Composition to Stop Burn Wound Progress

|  | % w/w |
| --- | --- |
| Ethanolic plant extracts | 10 |
| Ammonium hydroxide 10% solution | 2 |
| Ethyl alcohol | 22 |
| Carbomer | 1 |
| DDW | 65 |

Example 3

Composition to Stop Burn Wound Progress

|  | % w/w |
| --- | --- |
| Ammonium hydroxide 10% solution | 3 |
| Alcoholic *Aloe Vera* Gel | 57 |
| CARBOPOL ® 934 | 1 |
| Purified water to | 100% |
| Total ethanol | 20% |

Example 4

Composition to Stop Burn Wound Progress

|  | % w/w |
| --- | --- |
| *Passiflora* extract | 5 |
| 10% Ammonium hydroxide soln | 3 |
| Urea | 1 |
| Ethanol | 35 |
| Polyacrylate | 1 |
| Glycerol | 7 |
| DDW | 48 |

Example 5

Composition to Stop Burn Wound Progress

|  | % w/w |
| --- | --- |
| Ethyl alcohol | 30 |
| Carbomer | 2 |
| Ammonium hydroxide 10% sol | 4 |
| Distilled water to | 100 |

Example 6

Composition to Stop Burn Wound Progress

Ethanolic plant extracts in
Alcohol containing Gel base
Where the concentration of ethanol is 60% w/w

Example 7

Composition to Stop Burn Wound Progress

|  | % w/w |
| --- | --- |
| Ethanol | 22% |
| CARBOPOL ® 934 | 2.2% |
| Ammonium hydroxide 10% solution | 4% |
| DDW | 71.8% |

The preparation was applied and remained on the injury for 20 minutes, on a very thick layer, on the a surface of about 5 centimeters square of the arm of a man aged 35, injured by boiling water. The pain was completely relived after application of the composition in example 7. No vesicles or wound developed after this treatment.

Example 8

Composition to Stop Burn Wound Progress

|  | % w/w |
| --- | --- |
| Ethanol | 30% |
| CARBOPOL ® | 2% |
| Ammonium hydroxide 10% solution | 4% |
| Plant extracts | 7% |
| Plant tinctures | 1% |

Example 9

Composition to Stop Burn Wound Progress

|  | % w/w |
| --- | --- |
| Ethanol | 20% |
| CARBOPOL ® | 2.5% |
| Ammonium hydroxide 10% solution | 4% |
| Plant tinctures | 5% |
| Purified water | 68.5% |

Example 10

Composition to Stop Burn Wound Progress

|  | % w/w |
| --- | --- |
| Ethanol | 45% |
| CARBOPOL ® | 2% |
| Ammonium hydroxide 10% solution | 4% |
| Triethanolamine | 1% |
| Plant tinctures | 5% |
| Purified water | 43% |

Example 11

Composition to Stop Burn Wound Progress

|  | % w/w |
| --- | --- |
| Ethanol | 20 |
| CARBOPOL ® | 1.5 |
| Ammonium hydroxide 10% solution | 3 |
| DDW | 68.5 |

Example 12

The Effects of the Treatment on Wound Histology and Burn Depth After Heat Burn

The aim of the experiment was to measure the effect of the treatment on wound histology and burn depth after heat burn:

Standardized partial thickness burns were inflicted on the back shaved (24 hours before the experiment) of Sprague Dawley rats by using a copper cylinder, (R=1 cm, H=1 cm, W=100 g), heated to 75° C. in a water bath.

The composition of Example 5 was applied, to an area larger than the injury, immediately after the burn or one hour after. Following the treatment, the rats were sacrificed and the wound as well as adjacent normal tissues were sampled, fixed, processed by routine technique and stained with hematoxylin & eosin. The progress of the wound was assessed at various times and compared with untreated control groups. The effect of the treatment on preventing the burn progress was evaluated by measuring the burn depth by using a program for evaluation of the vascular network damage and by histological analysis of skin anatomic elements. The data were analyzed by ANOVA test.

Animal experiments complied with animal care regulations.

EXPERIMENTAL RESULTS

The progress of the burn damage was prevented or reduced significantly in rats treated with the composition described in Example 5 stored previous to the experiment at +5° C.

FIG. 1 shows histological images of rat skin structures (collagen, epidermis, muscles) after the thermal burn, with (FIG. 1B-D) and without (FIG. 1A) treatment.

Example 13

Compositions were applied to the burn skin inflicted as previously described (example 12):
The following compositions were used:
CARBOPOL® delivery systems in a gel form containing ethanol in concentrations from 20 to 63% w/w.
Spray liquids containing ethanol in concentrations from 20 to 70% w/w in an aqueous medium.
Burn Progress Assessment:
Burn progress was assessed by measuring the burn depth by using a program—Galay CUE 2—for evaluation of vascular network damage.

The histological burn depth was calculated by measuring the level of blocked and patent vessels within the burn specimens. Histological tissue sections were taken from burn area. The depth of the deepest blocked vessel and that of the most superficial undamaged vessel were measured microscopically from the surface of the burn, using Galay CUE2 advanced software. The resulting values were expressed as a percentage of the total skin thickness, the mean of which was considered to be the percentage depth of the burn. These assessments were made at 3, 6 and 24 hours after the burn. These measurements were expressed as a percentage (%) of the total skin thickness.

FIG. 2 demonstrates measurement of depth dermal microvascular destruction in the first 24 hours (at 3, 6 and 24 hours) after burn infliction: Animals have been treated immediate after infliction with CARBOPOL® gels containing 20, 30, 50 and 63% w/w ethanol and 1 hour after infliction with the gel containing 30% ethanol. The results are compared with untreated inflicted rats. The depth parameter was measured in rats sacrificed 3, 6, and 24 hours after burn infliction.

Results in FIG. 2 show parameters measured at 3, 6 and 24 hours after skin burn: treatment with CARBOPOL® gels containing 20-63% w/w ethanol drastically impeded the micro-vascular destruction and progress of burn as compared to untreated rats inflicted animals immediately. Treatment one hour after infliction with 30% w/w ethanolic gel was also very efficient.

Histological Analysis of Skin Anatomic Elements:
After the treatment, the animals were sacrificed and the wound as well as adjacent normal tissues were sampled, fixed, processed by routine techniques and stained with hematoxylin & eosin. The parameters investigated included edema formation, inflammation cells migration and preservation of skin structures (epidermis, basal layer, collagen, muscles and appendages). Every histological parameter has been scored using a scale from 0 to 4. Numbers express the balance between the damaged and preserved parameters. A normal parameter is has a score of "0". With increasing damage, the parameter is represented by higher numbers. Number "4" represents total damage. The sums of all scored parameters express the preservation or destruction of the skin after thermal burn for every treatment. The scored number representing total damage is "28" These assessments were made at 3, 6 and 24 hours after burn infliction.

Figure 3:
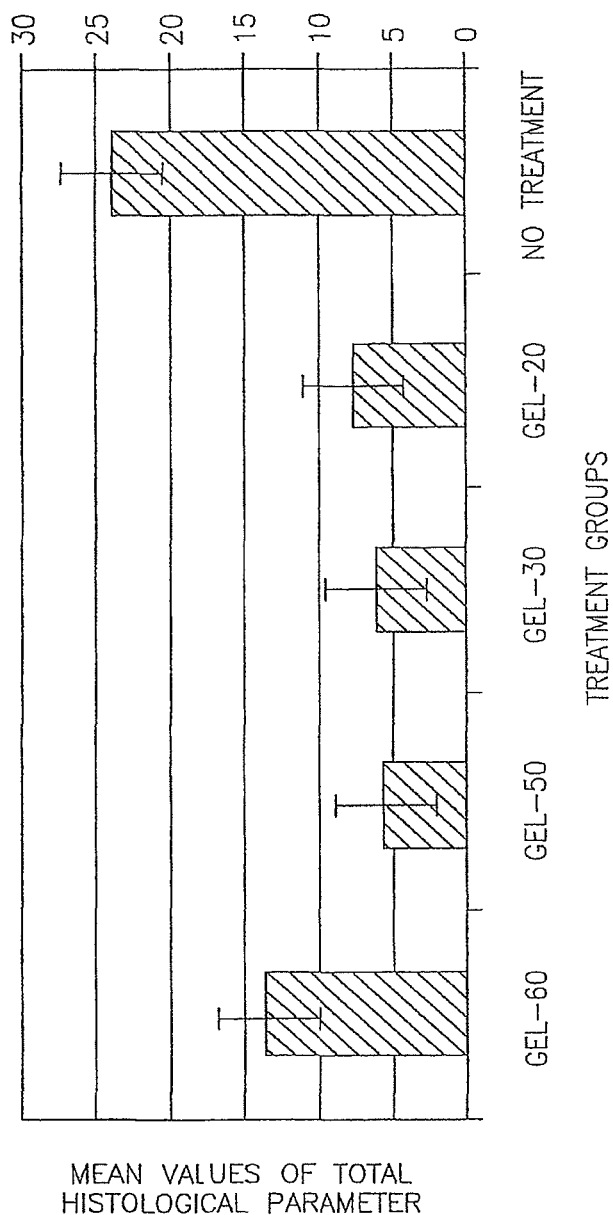
FIG. 3 shows histological parameters from skin sections 24 hours after burn infliction. The rats were treated immediate after infliction with gels containing 20, 30, 50 and 60% ethanol.

FIG. 3 shows histological parameters from skin sections 24 hours after burn infliction.

FIG. 3 clearly shows that treatment with gels containing ethanol stopped burn progression—the most effective gel had a parameter value of 5 as compared with 24 for untreated animals in which the burn wound progressed.

In these experiments preparations and delivery systems containing ethanol between 20 to 50% were the most effective in stopping burn progression.

Figure 4:
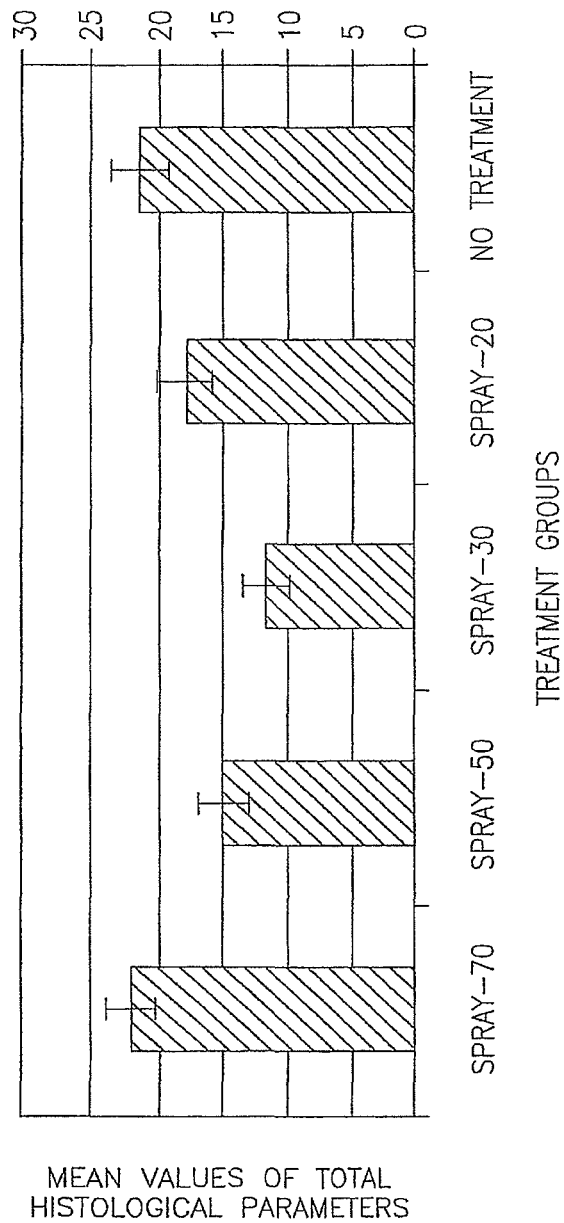
FIG. 4 shows histological parameters from skin sections, 24 hours after burn infliction. The rats were treated immediate after infliction with liquid sprays containing 20, 30, 50 and 70% ethanol.

FIG. 4 Inflicted rats were treated with liquid sprays containing 20, 30, 50 and 70% ethanol. Results indicate that at 70% the wound burn continued to develop as in control untreated rats, while some affect was measured at lower alcohol concentrations.

Example 14

In this experiment heat burns were inflicted as previously described in 14 rats. Two rats served as control and the other animals (4 groups of 3 rats each.) were immediately treated as follows:
Control—untreated
Group 1—"Cool gel" composed of polymeric gel in water
Group 2—15% w/w ethanol in 2.2% CARBOPOL® gel comprising 2.2% carbopol 934P, 4% ammonium hydroxide 10% solution and water.
Group 3—30% w/w ethanol in a carbopolic gel composing 2.2% CARBOPOL® 934P, 4% ammonium hydroxide 10% solution and water.
Group 4—60% w/w ethanol in a carbopolic gel composing 2.2% CARBOPOL® 934P, 4% ammonium hydroxide 10% solution and water.
Mean value histological parameters assessed TABLE-US-00011 Control-23 Group 1-19 Group 2-17 Group 3-5 Group 4-17

The results of this experiment indicate that compositions containing ethanol and ammonium hydroxide were efficient in impeding the burn development as compared to controls-untreated or aqueous gels treated animals.

Example 15

| Stop Burn Cream | |
| --- | --- |
| Vegetable oil | 8% |
| Lecithin | 0.4% |
| Tween 20 | 2.2% |
| Span 20 | 1% |

-continued

Stop Burn Cream

| | |
|---|---|
| CARBOPOL ® 980 | 2% |
| Ethanol 96 | 35% |
| Ammonium hydroxide 10% | 2% |
| Water to | 100% w/w |

Example 16

Stop Burn Cream with Aromatic Oils

| | |
|---|---|
| Aromatic oil | 5% |
| Tween 20 | 4% |
| Span 20 | 7% |
| CARBOPOL ® 980 | 2% |
| Ethanol 96 | 35% |
| Ammonium hydroxide 10% | 2% |
| Water to | 100% |

Example 17

| | % w/w |
|---|---|
| Ethanol 96 | 20 |
| CARBOPOL ® 934 | 2.2 |
| Ammonium hydroxide 10% solution | 4 |
| DDW | 71.8% |

The composition is refrigerated before use, and is applied as very thick layer on the burned area.

Example 18

Effect of Compositions of the Present Invention on Skin Burned in the Rat
Method
The dorsal skin of rats was shaved 24 hours before the start of the experiment.
Burn injury: 75.degree. C./3 sec by 100 g cupper cylinder.
Animals: male SD rats (250-300 g)
Compositions:
Gel: Ethanol 95 30%, CARBOPOL® 934 2.2%, Sol Ammonium hydroxide (10%) 4.4, Distilled water to 100% w/w.
Treatment:
Gel application (one thick layer) immediately after the burn was inflicted. The gel was left on skin for 40-45 min.

| Treatment Group | Number of Rats in each group |
|---|---|
| No Treatment | 2 |
| Gel Treatment | 2 |

Figure 5A:
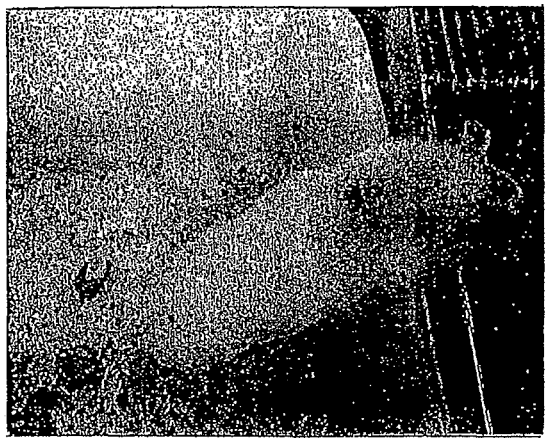
FIG. 5 shows the effect of the compositions of the invention on the development of skin burns in the rat.
Figure 5B:

The results are shown in FIGS. 5a, 5b respectively, from which it may be seen that treatment with compositions of the present invention resulted in clinical healing of the wounds 24 hours after the burn injury.

The invention claimed is:

1. A method for treating a burn, the method comprising applying to the burned area a composition in the form of a gel, comprising ethyl alcohol and a topically acceptable polymeric carrier which forms a gel-like matrix with said ethyl alcohol, wherein the concentration of ethyl alcohol is in the range of 20-50% based on the total weight of the composition, and the treatment impedes micro-vascular destruction and progression associated with the burn.

2. The method according to claim 1, wherein the polymeric carrier comprises an acidic polymer or a salt thereof.

3. The method according to claim 2, wherein the acidic polymer is an acrylic polymer.

4. The method according to claim 3, wherein the acrylic polymer is a carbomer.

5. The method according to claim 3, wherein the acrylic polymer is at least partially neutralized with a base.

6. The method according to claim 5, wherein the base is a nitrogen containing base.

7. The method according to claim 6, wherein the base is selected from the group consisting of ammonium hydroxide, dialkanolamines and trialkanolamines.

8. The method according to claim 7, wherein the concentration of ethanol is from 20% to 50%, the concentration of acrylic polymer is from 0.05% to 5% and the base is ammonium hydroxide at a concentration of from 0.1% to 10%.

9. The method according to claim 7, wherein the concentration of ethanol is from 20% to 50% w/w, the concentration of acrylic polymer is from 0.05% to 5% and the base is triethanolamine at a concentration of 0.1% to 6%.

10. The method according to claim 1, wherein the composition further comprises urea.

11. The method according to claim 1, wherein the composition further comprises plant derived material.

12. The method according to claim 11, wherein the plant derived material is in the form of one or more plant extracts, one or more tinctures, one or more oils and/or one or more macerates.

13. The method according to claim 12, wherein the plant is selected from the group consisting of *arnica, plantago, equisetum*, lavender, joubarbe, *hamamelis, urtica, calendula, daucus, symphytum, sanguisorba, symphytum, aloe vera*, roman chamomile, tea tree, witch hazel, Emu, Celosia Argentea and *mameluca*, and combinations thereof.

14. The method according to claim 1, wherein the composition further comprises one or more ingredients selected from the group consisting of a local anesthetic, antibiotic, plant extract, vitamin, growth factor, protein, histamine, carnosine, insulin, antiinflammatory agent, antiseptic agent, antifungal agent, anticytokine, an interleukin, growth hormone and re-epithelization factors, and combinations thereof.

15. The method according to claim 1, wherein the topically acceptable carrier comprises chitin, guar, chitosan, polyvinylpyrrolidone, polyvinylalcohol, gum, silastic, eudragit, pectin, hyaluronic acid, hyaluronate, gelatin, gelatin derivative, agar, polymer adhesives, polaxomers, methylcelluose, ethylcellulose, hydroxypropylcellulose, hydroxyethylcellulose, or a mixture thereof.

16. The method of claim 1, wherein the burn is caused by a scald.

17. The method of claim 1, wherein the burn is a second degree burn.

18. The method of claim 1, wherein the concentration of ethyl alcohol in the composition is from 20% to 40%.

19. The method of claim 1, wherein the concentration of ethyl alcohol in the composition is about 20%.

20. The method of claim 1, wherein the concentration of ethyl alcohol in the composition is about 30%.

21. The method of claim 1, wherein the concentration of ethyl alcohol in the composition is about 35%.

22. The method of claim 1, wherein the concentration of ethyl alcohol in the composition is about 40%.

23. The method of claim 1, wherein the concentration of ethyl alcohol in the composition is about 45%.

24. The method of claim 1, wherein the concentration of ethyl alcohol in the composition is about 50%.

25. The method of claim 1, wherein the composition is applied within about one hour of burn onset.

26. The method of claim 1, with the proviso that the composition is free of local anesthetic.

* * * * *